United States Patent
Ettlinger et al.

(10) Patent No.: US 6,811,748 B2
(45) Date of Patent: Nov. 2, 2004

(54) SYSTEM FOR AND METHOD OF STERILIZATION OF OBJECTS

(76) Inventors: Eugene Ettlinger, 2575 Palisades Ave., Riverdale, NY (US) 10463; Shirley Basso, 319 Ferndale Blvd., Islip, NY (US) 11751

( * ) Notice: Subject to any disclaimer, the term of this patent is extended or adjusted under 35 U.S.C. 154(b) by 0 days.

(21) Appl. No.: 10/375,984

(22) Filed: Feb. 28, 2003

(65) Prior Publication Data

US 2004/0170525 A1 Sep. 2, 2004

(51) Int. Cl.[7] ................................................ A61L 2/10
(52) U.S. Cl. .................................. 422/24; 250/455.11
(58) Field of Search ...................... 422/24; 250/455.11; 312/6, 31.1, 265.4, 265.5; 135/96, 141, 157, 161, 117; 52/79.5

(56) References Cited

U.S. PATENT DOCUMENTS

| | | | | |
|---|---|---|---|---|
| 4,304,224 A | * | 12/1981 | Fortney | 600/21 |
| 4,675,923 A | * | 6/1987 | Ashley | 4/599 |
| 4,706,551 A | * | 11/1987 | Schofield | 454/66 |
| 5,225,172 A | * | 7/1993 | Meyler et al. | 422/300 |
| 5,645,480 A | * | 7/1997 | Spengler | 454/187 |
| 5,908,043 A | * | 6/1999 | Paes et al. | 135/139 |
| 5,958,336 A | * | 9/1999 | Duarte | 422/24 |
| 6,231,819 B1 | * | 5/2001 | Morello | 422/186.3 |
| 2003/0037812 A1 | * | 2/2003 | Stewart et al. | 135/96 |

* cited by examiner

Primary Examiner—E. Leigh McKane
(74) Attorney, Agent, or Firm—I. Zborovsky

(57) ABSTRACT

For sterilization of objects a plurality of sources of ultraviolet light emission are arranged in an enclosure formed so as to enclose an object to be sterilized with the sources of ultraviolet light emission emitting light in an inner chamber of the enclosure onto an object to be sterilized.

21 Claims, 3 Drawing Sheets

US 6,811,748 B2

SYSTEM FOR AND METHOD OF STERILIZATION OF OBJECTS

BACKGROUND OF THE INVENTION

The present invention relates to a system for and a method of sterilization of objects.

Sterilization of objects with the use of ultraviolet light is known. The sterilization is performed in these cases by irradiation of objects With ultraviolet light produced by ultraviolet sources which generate ultraviolet light emission. The sources of the ultraviolet light are usually arranged close to objects to be sterilized, and then activated to carry out the sterilization process. It is believed that the existing systems and methods can be further improved.

SUMMARY OF THE INVENTION

Accordingly, it is an object of the present invention to provide a system for and a method of sterilization of objects which are further improvements of the existing systems and methods.

In keeping with these objects and with other which will become apparent hereinafter, one feature of the present invention resides, briefly stated, in a system for sterilization of objects, which includes a plurality of sources of ultraviolet light emission; and an enclosure which is formed so as to completely enclose the object and form an inner chamber therein, wherein the sources of ultraviolet light emission are arranged inside the enclosure in the inner chamber and oriented to direct the ultraviolet light emission toward an object to be sterilized.

In accordance with another feature of the present invention, a method of sterilizing objects is proposed which includes the steps of providing a plurality of sources of ultraviolet light emission, enclosing an object to be sterilized with an enclosure, and arranging, the sources of ultraviolet light radiation in an inner chamber of the enclosure so as to emit light in the inner chamber onto an object to be sterilized.

When the system is designed and the method is performed in accordance with the present invention, a highly efficient sterilization of objects is carried out which efficiently kills bacteria and prevent infections.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
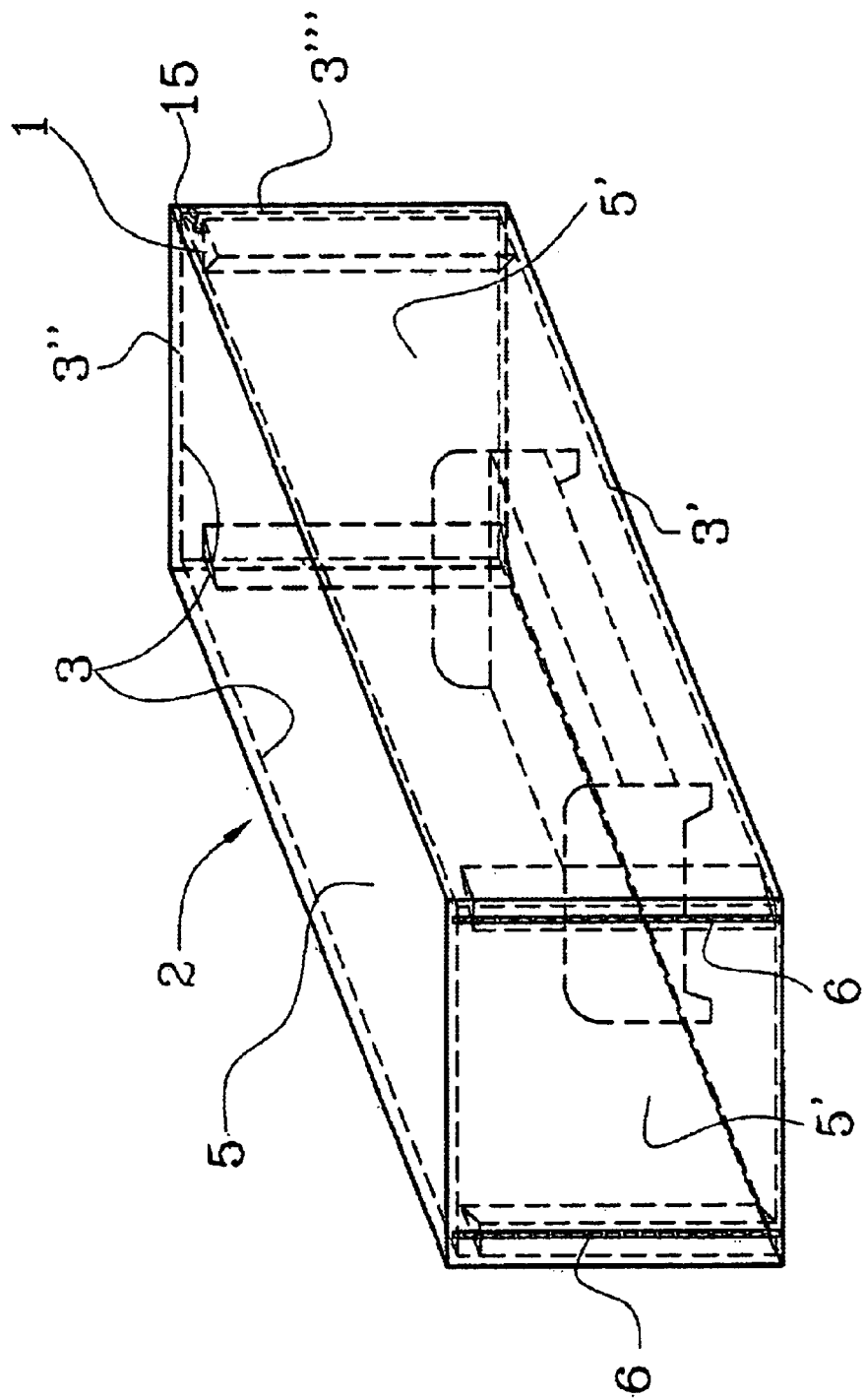
FIG. 1 is a perspective view of a system for sterilization of objects which implements a method of sterilization in accordance with the present invention.

A system for sterilization of objects in which a method of sterilization of objects can be performed in accordance with the present invention is shown in general in FIG. 1. The inventive system includes a plurality of sources of ultraviolet light emission each identified with reference numeral 1. The system further includes an enclosure which is identified as a whole with reference numeral 2. The sources of ultraviolet light emission 1 are located inside the enclosure 2 in an inner chamber which is enclosed by the enclosure.

Figure 6:
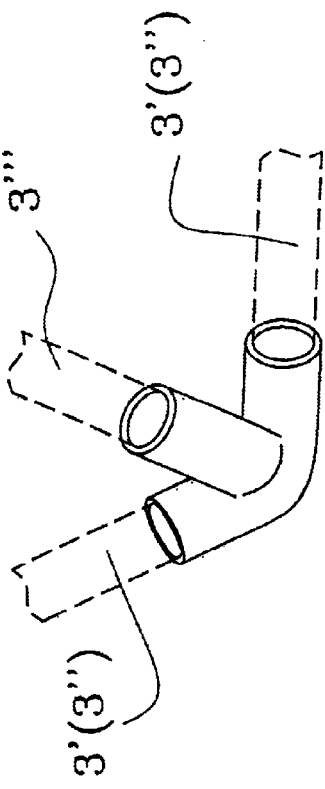
FIG. 6 is a view showing connections of elements of the inventive system.
Figure 4:
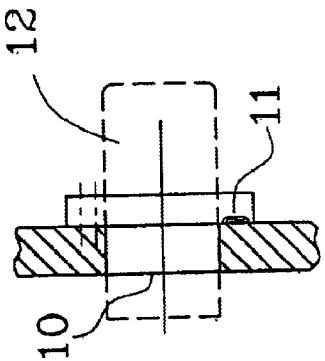
FIG. 4 is a view showing a fragment of the inventive system in accordance with another embodiment of the present invention.

The enclosure 2 has a frame which is identified with reference numeral 3, and preferably is composed of a plurality of pipes. The frame includes four bottom pipes 3', four top pipes $3'_C$ and four vertical pipes $3''_C$. Also intermediate pipes 3'' can be provided as well. The pipes are connected by a connecting elements 4 arranged on the corners of the enclosure. Each connecting element 4, as shown for example in FIG. 6, can be formed as a fitting which has three short pipe-shaped receptacles. The ends of the pipes 3', $3'_C$, $3'_{CC}$ are inserted and tightly but releasably held in the receptacles for example by friction between the outer surfaces of the pipes and the inner surfaces of the receptacles. In order to adjust the size of the enclosure to the size of an object to be sterilized, the pipes 3', $3'_C$, $3'_{CC}$ can be formed as telescopable pipes each composed of two pipe pieces which are telescopably movable in one another, so that the total length of the corresponding pipe can be increased or reduced.

Figure 2:
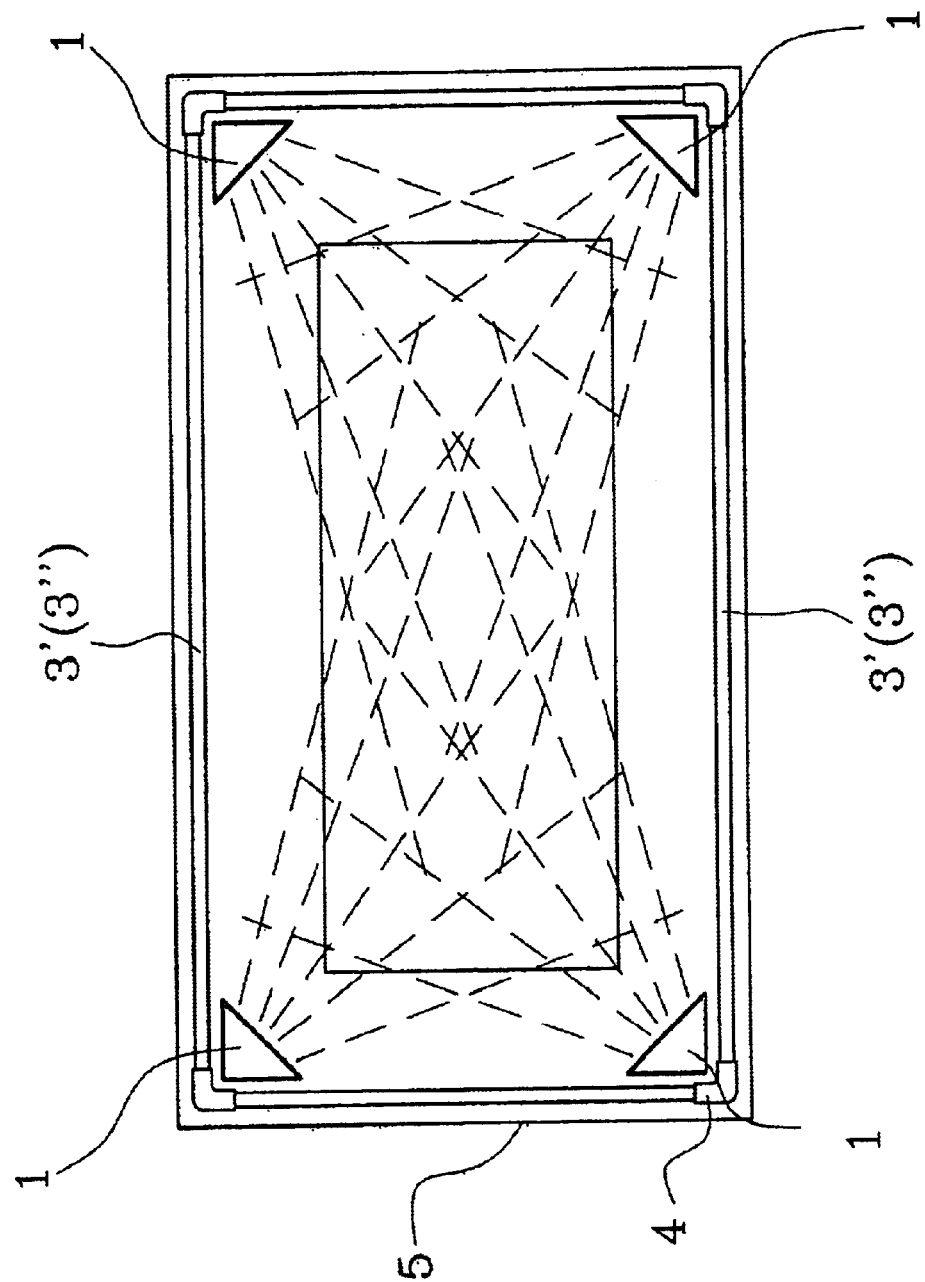
FIG. 2 is a plan view of the inventive system for sterilization of objects.

A covering material 5 is fitted on the frame 3 in its assembled condition. The cover material can be fabric, or another material which protects the interior of the enclosure and confines the UV radiation or bactericidal fluid inside the enclosure. The covering material forms vertical walls and a top of the receptacle 2. As shown in FIGS. 1 and 2, adjacent vertical walls are preferably at substantially right angles to each other The side flaps 5' of the material which form the side walls can be connected with one another, for example by zippers 6. For the operation of the system the zippers are closed to form the each composed vertical walls interconnected which limit the inner chamber of the enclosure. For providing access to the interior of the enclosure, the corresponding zippers are open and the side flap which forms a wall can be rolled up and placed on the top flap of the material.

Each source of ultraviolet light emission 1 can include for example a fluorescent central tube 7, a flat reflector 8 located behind the tube, a substantially triangular casing 9, and a not shown transformer through which the source 1 is connected to an electrical power supply. The sources of ultraviolet light emission 1 are arranged in the corners of the enclosure so that two sides of each source 1 extend substantially parallel to the two walls which form the corresponding corner, while the flat reflector extends between these sides as shown, for example, in FIG. 2.

The system in accordance with the present invention operates in the following manner. When it is necessary to sterilize an object for example a hospital bed, the frame 3 is assembled of the pipes 3', 3'', 3''' connected by the connecting elements 4 as shown in FIG. 1. Then the material 5 is placed on the frame and the side flaps are unrolled and fall down, and thereafter are connected with one another by zippers 6 so as to form the enclosure 2 around the bed. At the lower side the floor or the surface on which an object, for example a hospital bed is placed closes the inner chamber of the enclosure from below. The sources of ultraviolet light radiation 1 are placed in the corners of the enclosure 2 and connected to an electric power supply. The sources 1 emit ultraviolet radiation into the inner chamber of the enclosure as shown in FIG. 2. As a result, all surfaces of the object, in particular of the hospital bed shown in FIG. 1, are sterilized and bacteria are killed.

In the event if there is an enclosed space which has to be sterilized, for example a room, the sources 1 of ultraviolet light emission can be placed in the corners of the room or in the center at 90° angles.

The frequency and the intensity of the ultraviolet radiation for sterilization purposes is known in the art and therefore it is believed to be unnecessary to provide corresponding details of these parameters.

After the cycle of irradiation, the zippers 6 are opened, the side flaps of the enclosure are rolled up onto the top flap, and the material 5 is removed, the frame 3 is disassembled, and the thusly folded enclosure together with the sources of ultraviolet light radiation can be stored in a corresponding place or in a mobile container for transporting to a next object.

In accordance with another embodiment of the present invention, the walls of the enclosure can be provided with windows 10 which are closeable by covers 11 attached at one side to the material 5 and having for example a VEL-CRO or hook and loop fastener connection at the opposite side. A source of a batericidal fluid, for example a spraying nozzle connected with a container, can be introduced in the window 10 and the bactericidal fluid is supplied into the inner chamber of the enclosure 2. The bactericidal fluids are generally known in the art and can be formed as sprays, gasses, etc. The treatment with bactericidal fluid can be performed in addition to the treatment with the ultraviolet light emission, or separately from it.

As can be seen from the drawings, the windows 10 are provided in the longer walls. In each wall there are windows spaced horizontally from one another, cover the whole length of the inner space. Also, there are lower windows to treat an area under the bed, and upper windows to treat an area above the bed.

Figure 5:
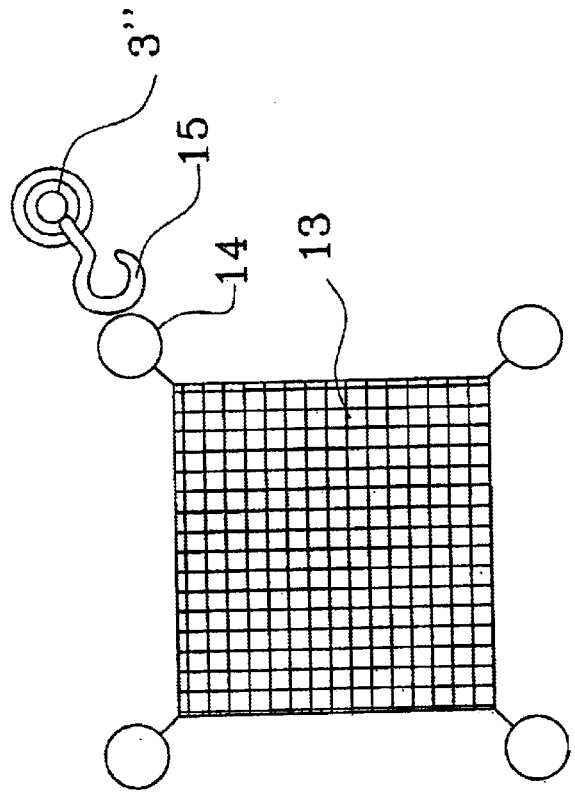
FIG. 5 is a view showing a further embodiment of the present invention.
Figure 3:
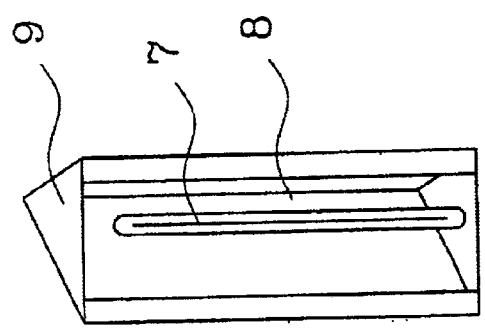
FIG. 3 is a view schematically showing a source of ultraviolet light emission.

In accordance with a further embodiment shown In FIG. 5, the enclosure can be provided with an additional supporting element for placing small objects on it and their sterilization in the inner chamber of the enclosure 2. A supporting element is shown in FIG. 5 and identified with reference numeral 13. It can be formed for example of a net-like material and provided with loops 14 at its corners, while the vertical pipes 3" of the frame 3 can be provided with hooks 15 arranged at a certain height. The supporting element 13 can be positioned inside the enclosure 2 and its loops 14 can be connected with the hooks 15 of the pipes of the frame. Thereafter corresponding objects, for example medical instruments, devices, etc. can be placed on the supporting element 13.

When the sources of ultraviolet light emission are activated, the ultraviolet light sterilizes the objects placed on the supporting element 13, which objects are readily accessible because of the net-like structure of the supporting element 13. It is to be understood that there can be more supporting elements 13 placed at different heights in the inner chamber of the enclosure 2.

It will be understood that each of the elements described above, or two or more together, may also find a useful application in other types of methods and constructions differing from the types described above.

While the invention has been illustrated and described as embodied in system for and method of sterilization of objects, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A system for sterilization of objects, comprising a plurality of sources of ultraviolet light emission; and an enclosure formed so as to enclose an object and to form an inner chamber in which the object to be sterilized can be located, said enclosure having vertical walls wherein adjacent walls are positioned at substantially right angles to one another forming a corner between each two of said adjacent walls, said sources of ultraviolet light emission being arranged in said inner chamber so as to emit light in said inner chamber of said enclosure onto an object to be sterilized, each of said sources of ultraviolet light emission having a substantially triangular casing with two sides extending substantially parallel to the walls forming a corresponding one of the corners of the enclosure, an ultraviolet light emitting element, and a substantially flat reflector extending between said two sides and directing the ultraviolet light from a respective one of said corners of said enclosure onto the object.

2. A system as defined in claim 1, wherein said enclosure has a frame, and a material covering said frame.

3. A system as defined in claim 2, wherein said frame has a plurality of horizontal pipes forming a lower part of the frame, a plurality of horizontal pipes forming an upper part of the frame, and a plurality of vertical pipes connecting said pipes of said upper part and said lower part of the frame with one another.

4. A system as defined in claim 1, and further comprising connecting elements for connecting said pipes with one another.

5. A system as defined in claim 3, wherein each of said connecting elements has three pipe-shaped receptacles for receiving one of said vertical pipes and two of said horizontal pipes.

6. A system as defined in claim 2, wherein said material has a top substantially horizontal flap and a plurality of vertical, flaps connected with one another; and further comprising means for connecting said vertical flaps with one another.

7. A system as defined in claim 6, wherein said means for connecting said vertical flaps with one another include zippers.

8. A system as defined in claim 1, wherein at least one of said vertical walls has a plurality of windows for insertion of a unit providing a bactericidal treatment, said windows being spaced from one another in a horizontal direction and in a vertical direction.

9. A system as defined in claim 8, and further comprising a unit for providing a bactericidal treatment and inserted in at least one of said windows.

10. A system as defined in claim 8, and further comprising a covering element for covering said window in position non-use and opening said window for insertion of the bactericidal element, said covering element having one end fixedly connected with said at least one vertical wall of the enclosure and another end provided with a hook and loop fastener for a releasable connection with said at least one vertical wall.

11. A System as defined in claim 1; and further comprising a supporting element for supporting objects in said inner chamber of said enclosure.

12. A system as defined in claim 11, wherein said supporting element is composed of a net-like material.

13. A system as defined in claim 11, wherein said supporting element has a plurality of loops arranged on its periphery, said enclosure having a frame with a plurality of vertical pipes provided with hooks on which said loops can be fitted for fixing said supporting element.

14. A system as defined in claim 12, wherein said frame has a plurality of pipes, said pipes being telescopable so as to adjust a size of the enclosure.

15. A system as defined in claim 1, wherein said enclosure has corner areas, said sources of said ultraviolet light emissions being arranged in said corner areas.

16. A method of sterilization of objects, comprising the steps of providing a plurality of sources of ultraviolet light emission; enclosing an object to be sterilized within an enclosure having an inner chamber; arranging said sources of ultraviolet light radiation in said inner chamber of said enclosure to emit ultraviolet light onto an object to be sterilized; forming said enclosure as an enclosure having vertical walls, wherein adjacent walls are positioned at substantially right angles to each other with a corner between each two of said adjacent walls; providing the sources of ultraviolet light radiation having a substantially triangular casing with two sides, an ultraviolet light emitting element, and a substantially flat reflector directing the ultraviolet light onto the object; placing each of the sources of ultraviolet light emission in a respective one of said corners so that the two sides of each of the sources of ultraviolet light emission extend substantially parallel to the walls of the enclosure in each of the corners, while the flat reflector extends between the two sides; and directing the ultraviolet light onto the object from respective one of the corners of the enclosure.

17. A method as defined in claim 16; and further comprising assembling a frame of a plurality of horizontal pipes forming a lower part of the frame, a plurality of horizontal pipes forming an upper part of the frame, and plurality of vertical pipes connecting said upper part and said lower part of the frame with one another.

18. A method as defined in claim 17; and further comprising covering the frame with a material which has a top substantially horizontal flap and a plurality of vertical flaps connected with one another; and connecting said vertical flaps with one another by zippers.

19. A method as defined in claim 16; and further comprising providing a window in the enclosure, and inserting through the window a unit for providing a bactericidal treatment.

20. A method as defined in claim 16; and further comprising supporting additional objects on a supporting element in said inner chamber of said enclosure, and sterilizing the additional objects supported on said supporting element by said sources of ultraviolet light emission.

21. A method as defined in claim 17; and further comprising forming the pipes of the frame telescopable so as to adjust a size of the enclosure.

\* \* \* \* \*